(12) United States Patent
Tsai et al.

(10) Patent No.: US 10,626,067 B1
(45) Date of Patent: Apr. 21, 2020

(54) PROCESSES FOR SEPARATING PARA-XYLENE FROM TOLUENE

(71) Applicant: UOP LLC, Des Plaines, IL (US)

(72) Inventors: Robert E. Tsai, Arlington Heights, IL (US); Joseph Montalbano, Elmhurst, IL (US); Ellen Arnold, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/408,806

(22) Filed: May 10, 2019

(51) Int. Cl.
    *C07C 7/09*     (2006.01)
    *B01D 3/00*     (2006.01)
    *C07C 2/86*     (2006.01)
    *B01D 3/14*     (2006.01)
    *C07C 7/00*     (2006.01)

(52) U.S. Cl.
    CPC ............... *C07C 7/09* (2013.01); *B01D 3/007* (2013.01); *B01D 3/14* (2013.01); *C07C 2/864* (2013.01); *C07C 7/005* (2013.01)

(58) Field of Classification Search
None
See application file for complete search history.

(56) References Cited

U.S. PATENT DOCUMENTS

| | | | | |
|---|---|---|---|---|
| 3,414,484 A | * | 12/1968 | Carson | B01D 1/2856 203/26 |
| 4,377,718 A | * | 3/1983 | Sato | C07C 2/864 585/467 |
| 5,744,687 A | * | 4/1998 | Ramachandran | C10G 70/046 208/103 |
| 2011/0092756 A1 | | 4/2011 | Lattner et al. | |
| 2012/0316375 A1 | * | 12/2012 | Zheng | C07C 2/864 585/450 |
| 2013/0253245 A1 | * | 9/2013 | Zheng | C07C 2/865 585/467 |
| 2015/0041307 A1 | | 2/2015 | Corradi et al. | |
| 2015/0087878 A1 | | 3/2015 | Laroche et al. | |
| 2015/0376087 A1 | | 12/2015 | Molinier et al. | |
| 2017/0073285 A1 | | 3/2017 | Whitchurch et al. | |
| 2018/0170842 A1 | | 6/2018 | Schmidt et al. | |
| 2019/0062239 A1 | | 2/2019 | Cheng et al. | |
| 2019/0062240 A1 | | 2/2019 | Cheng et al. | |
| 2019/0144358 A1 | | 5/2019 | Montalbano et al. | |

FOREIGN PATENT DOCUMENTS

WO     2017105848 A1     6/2017

\* cited by examiner

*Primary Examiner* — Philip Y Louie

(57) ABSTRACT

Processes and apparatuses for para-xylene separation. A stream of para-xylene is separated from a toluene stream in a fractionation column. An overhead stream of the fractionation column is compressed and then passed to a heat recovery zone to transfer heat from the overhead stream to another process stream in, for example, a heat exchanger. The fractionation column may be separating an effluent from a toluene methylation reactor.

16 Claims, 2 Drawing Sheets

PROCESSES FOR SEPARATING PARA-XYLENE FROM TOLUENE

FIELD OF THE INVENTION

Figure 1:
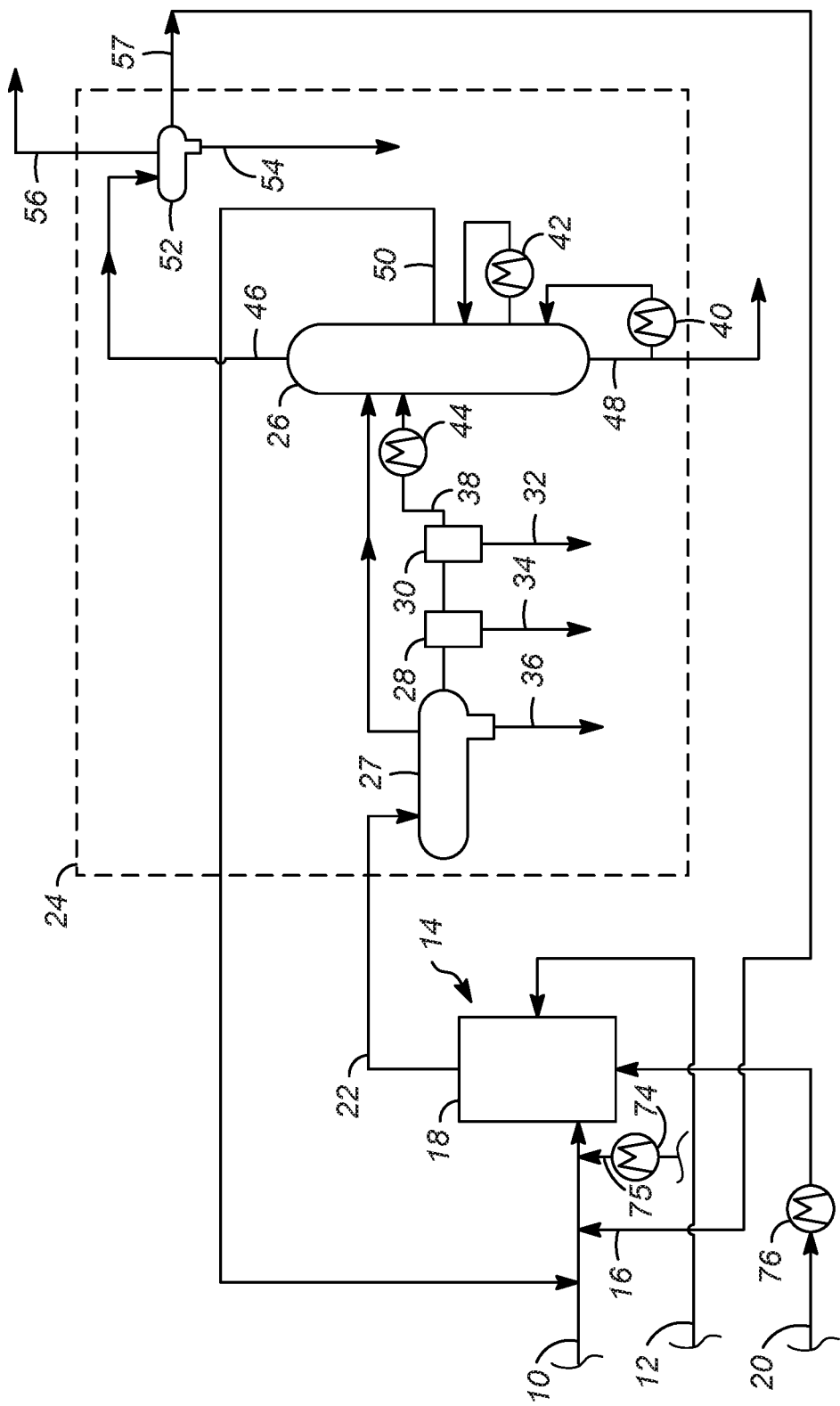

This invention relates to a process and apparatus for separating para-xylene, and more particular, to processes which separate para-xylene from toluene.

BACKGROUND OF THE INVENTION

Aromatics, particularly benzene, toluene, ethylbenzene, and the xylenes (ortho, meta, and para isomers), which are commonly referred to as "BTEX" or more simply "BTX," are extremely useful chemicals in the petrochemical industry. They represent the building blocks for materials such as polystyrene, styrene-butadiene rubber, polyethylene terephthalate, polyester, phthalic anhydride, solvents, polyurethane, benzoic acid, and numerous other components. Conventionally, BTEX is obtained for the petrochemical industry by separation and processing of fossil-fuel petroleum fractions, for example, in catalytic reforming or cracking refinery process units. The different aromatic compounds can be separated from each in an aromatic complex which has various separation units, as well as processing units for increasing the recovery of specific compounds.

Specifically, para-xylene and meta-xylene are important raw materials in the chemical and fiber industries. Terephthalic acid derived from para-xylene is used to produce polyester fabrics and other articles which are in wide use today. One process which is utilized to produce para-xylene is a toluene methylation process.

The toluene methylation process alkylates toluene using methanol to produce para-xylene at very high (90+%) selectivity relative to total xylenes. Fractionation of the reaction effluent is ultimately necessary to separate the components which include products of light ends, water, oxygenates and acids, benzene, unconverted toluene, xylenes, and heavier components. The separation may be achieved by first performing a "loose" split using a first fractionation column operated for light ends removal and crude recovery of para-xylene. The resulting product stream may then be routed to a second fractionation column, within a larger aromatics complex, for further separation of toluene from the desired xylene products. Alternatively, the xylene separation can be accomplished solely via a fractionation column, wherein practically all of the benzene and toluene are recycled internally so that the only terminal products are xylenes and heavier aromatics.

A disadvantage of the configuration with two columns, and the first one performing a "loose" split, is that oxygenates produced in the toluene methylation reaction that co-boil with toluene are given more opportunity to migrate and damage downstream units in the aromatics complex. For example, oxygenates may damage adsorbent in a para-xylene separation unit. This issue is especially a concern for para-xylene separation units that utilize toluene as a light-desorbent. One advantage, though, is that the first fractionation column is more amenable to heat integration within the aromatics complex versus the second fractionation column, due to its lower bottoms temperature.

However, either configuration necessitates substantially increased fractionation requirements (i.e., condenser and reboiler duties) in the fractionation columns to achieve desired or acceptable separation of toluene and xylene.

Therefore, there remains a need for an effective and efficient process for separation xylene from toluene. Additionally, it would be desired for such processes to reduce the risk of oxygenates migrating downstream.

SUMMARY OF THE INVENTION

One or more processes and apparatuses have been invented which provide an effective and efficient process for separation xylene from toluene. According to the present processes and apparatuses, a heat pump is incorporated into the fractionation column separating toluene from xylenes.

Generally, a compressed overhead stream may be used to partially reboil the fractionation column as well as for other heat recovery purposes, such as pre-heating feeds within the toluene methylation unit. Overall, the heat pump improves the energy efficiency of the fractionation column while at the same time enabling the configurational benefits mentioned above (i.e., limiting oxygenate migration).

Therefore, the present invention may be characterized, in at least one aspect, as providing a process for para-xylene separation by: alkylating, in a toluene methylation zone, toluene with methanol to provide a methylated effluent comprising para-xylene and toluene; separating, in a fractionation column, the methylated effluent into at least an effluent stream comprising para-xylene, a recycle stream comprising toluene, and an overhead stream comprising $C_1$-$C_6$ hydrocarbons; recovering para-xylene from the effluent stream comprising para-xylene in a para-xylene recovery zone; compressing, in a first compression zone, the overhead stream to provide a compressed overhead stream; and, after the overhead stream has been compressed, transferring heat from the compressed overhead stream.

The present invention may also be characterized, in one or more aspects, as providing a process for para-xylene separation by: passing a toluene stream to a toluene methylation zone; passing a methanol stream to the toluene methylation zone, the toluene methylation zone operated under conditions to convert toluene to para-xylene and provide a methylated effluent comprising para-xylene and toluene; passing the methylated effluent to a fractionation column configured to separate the methylated effluent into at least an effluent stream comprising para-xylene, a recycle stream comprising toluene, and an overhead stream; passing the effluent stream comprising para-xylene to a para-xylene recovery zone configured to provide a para-xylene product stream; passing the overhead stream to a compression zone configured to compress the overhead stream and provide a compressed overhead stream; and, passing the compressed overhead stream to a heat recovery zone configured to remove heat from the compressed overhead stream in at least one heat exchanger.

In one or more aspects the present invention may broadly characterized as providing an apparatus for separating para-xylene from toluene. The apparatus may include a fractionation column having an inlet and a plurality of outlets, and being configured to receive, via the inlet, a stream comprising toluene and para-xylene, to separate the stream, and to provide at least an effluent stream comprising para-xylene via a first outlet from the plurality of outlets, a recycle stream comprising toluene via a second outlet from the plurality of outlets, and an overhead stream via a third outlet from the plurality of outlets. The apparatus further may include a compression zone having configured to compress the overhead stream to provide a compressed overhead stream. The apparatus may also include a heat recovery zone comprising at least one heat exchanger configured to remove heat from the compressed overhead stream.

Additional aspects, embodiments, and details of the invention, all of which may be combinable in any manner, are set forth in the following detailed description of the invention.

DEFINITIONS

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, Ag, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally 50%, and preferably 70%, by mole, of a compound or class of compounds in a stream.

DETAILED DESCRIPTION OF THE DRAWINGS

Figure 2:
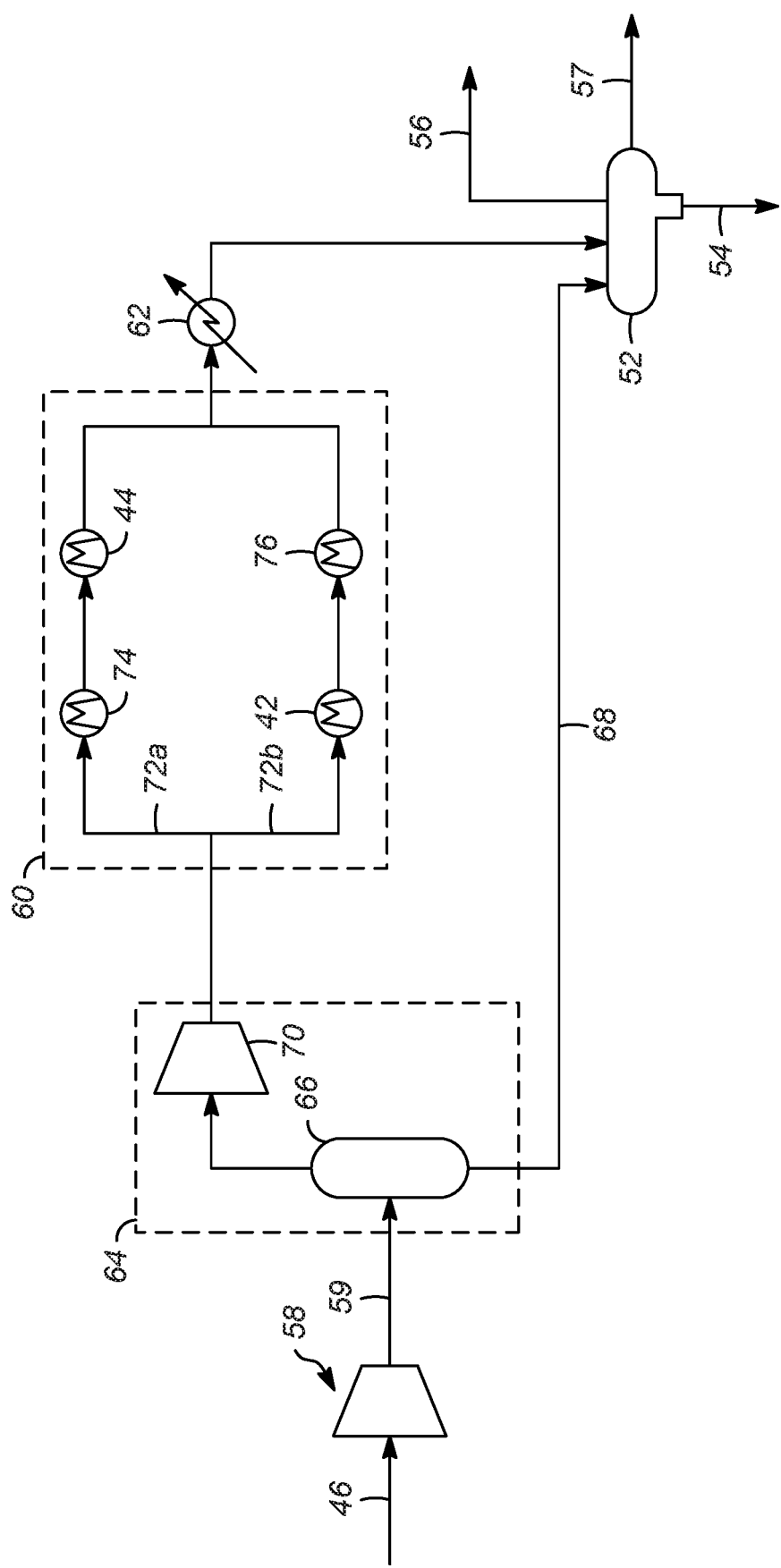

One or more exemplary embodiments of the present invention will be described below in conjunction with the following drawing figures, in which:

FIG. 1 shows a process flow diagram according to one aspect of the present invention; and, FIG. 2 shows a process flow diagram according to another aspect of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION OF THE INVENTION

As mentioned above, in the embodiments described herein, a heat pump is incorporated with the fractionation column separating toluene and xylenes. For example, two stages of compression may be used to attain sufficient driving force for exchange of the overhead stream with a side reboiler on the fractionation column. To maximize the energy recovery from the compression process, the overhead can be split as needed and allocated to other heat exchange zones, for example, pre-heating of water to the main toluene methylation injection and/or pre-heating of the liquid feed to the fractionation column. Consequently, a further benefit of the heat pump is a reduction of fuel requirements (fired heater duties) within the unit. As mentioned earlier, the fractionation results in a desirable separation (benzene/toluene confined to internal toluene methylation unit recycle and only xylenes and heavier species exiting the unit as net products) at the expense of a high energy requirement. The fractionation column is thus modified with a lower pump around that is heated via exchange with compressed column overhead. This supplemental heat offsets part of the main (bottoms) reboiling duty.

With these general principles in mind, one or more embodiments of the present invention will be described with the understanding that the following description is not intended to be limiting.

As shown in FIG. 1, a toluene stream 10, along with a methanol stream 12, is passed to a toluene methylation zone 14. The toluene stream 10 may be from a larger aromatic complex that receives a feed of alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. Such an aromatics-containing feed stream contains benzene, toluene and aromatics and typically contains higher aromatics and aliphatic hydrocarbons including naphthenes. The aromatics-rich feed may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. The reforming zone, as is known, generally includes a reforming unit that receives a feed. The reforming unit will typically comprise a reforming catalyst. Usually such a stream will also be treated to remove olefinic compounds and light ends, e.g., butanes and lighter hydrocarbons and preferably pentanes, such removal, however, is not essential to the practice of the broad aspects of this disclosure and is not shown. Although not depicted as such, a typical aromatics complex includes, for example, an aromatics extraction zone, a transalkylation zone, the toluene methylation zone 14, and a para-xylene extraction zone, and a xylene isomerization zone.

Returning to FIG. 1, the toluene stream 10 may be mixed with hydrocarbon from a recycle stream 16 (discussed below) before being injected into the toluene methylation zone 14. The toluene methylation zone 14 may be a fluidized bed reaction zone that includes a reactor 18 which receives the toluene stream 10, the methanol stream 12, and also a stream of lift water 20 which is used to fluidize or "lift"

catalyst and reactants upward through the reactor 18. The reactor 18 is operated under conditions, as are known, so that the toluene is alkylated with the methanol to produce xylenes.

A toluene methylation effluent stream 22 is passed to a separation zone 24 which includes, inter alia, a fractionation column 26 which has an inlet for receiving at least a portion of the toluene methylation effluent stream 22 and which separates the toluene methylation effluent stream 22. The separation zone 24 may also include other separation vessels 27, 28, 30 that produce water streams 32, 34, 36, some of which may include some methanol. A hydrocarbon stream 38 from the last vessel 30 is passed to the fractionation column 26.

As discussed above, the separation of the xylenes from the toluene is energy intensive. Accordingly, the fractionation column 26 may include a bottoms reboiler 40, a side reboiler 42, at least one exchanger 44 on one of the feed streams to the fractionation column 26. The fractionation column 26 provides an overhead stream 46, via a first outlet, comprising $C_1$-$C_6$ hydrocarbons, a bottoms stream 48, via a second outlet, and a sidedraw stream 50, via a third outlet, that may be recycled to the toluene methylation zone 14. The bottoms stream 48 includes para-xylene which may be sent to a para-xylene extraction unit (not shown) to recover the para-xylene.

According to the present processes, heat is recovered from the overhead stream 46 before the overhead stream 46 is separated in a vessel 52 into an aqueous stream 54, a fuel gas stream 56, and a liquid hydrocarbon stream 57 which includes toluene and which may be recycled to the toluene methylation zone 14 as the recycle stream 16 mentioned above. Thus, the energy efficiency of the separation within the fractionation column 26 is improved by recovering heat from the overhead stream 46.

Accordingly, as shown in FIG. 2, the overhead stream 46 is compressed in a first compression zone 58 having a compressor and then a compressed overhead stream 59 may be used to transfer heat in a heat exchange zone 60. From the heat exchange zone 60, a condenser 62 is used to cool the stream and then it is passed to the receiver vessel 52 (discussed above, see FIG. 1).

In an exemplary embodiment, the compressed stream 59 is passed to a second compression zone 64 having, for example, a knockout drum 66 which separates a liquid phase 68 from the compressed overhead stream before the compressed overhead stream is compressed further in a second compressor 70. The compressed overhead stream after the second compression zone 64 may be passed to the heat exchange zone 60. The liquid phase 68 from the knockout drum 66 may be passed to the vessel 52.

In an exemplary heat exchange zone 60, the compressed overhead stream is split into two or more portions 72a, 72b. A first portion 72a is passed to at least one heat exchanger, for example, a heat exchanger 74 for an aqueous recycle stream 75 (which can be formed from, for example, at least portions of aqueous streams 36, 54 separated from the toluene methylation effluent stream 22. See, FIG. 1. The first portion 72a may also be passed to the feed exchanger 44 for the fractionation column 26 (see, FIG. 1). A second portion 72b may be passed to the side reboiler 42 of the fractionation column 26 (see, FIG. 1), a lift water exchanger 76 (see, FIG. 1), or both. The depicted heat exchange zone 60 is merely exemplary and any number of portions of the compressed stream 59 and exchangers may be used.

As should be appreciated by those of ordinary skill in the art, the embodiments of the present invention provide an economical way to better balance the heat transfer and recovery within a toluene methylation unit, preferably within an aromatics complex, when there is rigorous product fractionation within the toluene methylation unit. The benefit may change for alternate feed scenarios or for situations where the overall energy balance of the complex is different.

According to a theoretical evaluation, the economic savings over two years would offset the initial investment costs associated with incorporating the additional equipment specified herein. This theoretical evaluation was based on a complex with approximately 1,700 KMTA para-xylene production from a 3,400 KMTA feed to the toluene methylation unit and 8,000 h/yr operation.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for para-xylene separation, the process comprising alkylating, in a toluene methylation zone, toluene with methanol to provide a methylated effluent comprising para-xylene and toluene; separating, in a fractionation column, the methylated effluent into at least an effluent stream comprising para-xylene, a recycle stream comprising toluene, and an overhead stream comprising $C_1$-$C_6$ hydrocarbons; recovering para-xylene from the effluent stream comprising para-xylene in a para-xylene recovery zone; compressing, in a first compression zone, the overhead stream to provide a compressed overhead stream; and, after the overhead stream has been compressed, transferring heat from the compressed overhead stream. An embodiment of the invention is one, any or all of prior embodiments in this paragraph up through the first embodiment in this paragraph further comprising before transferring heat from the compressed overhead stream, compressing the compressed overhead stream in a second compression zone, wherein the second compression zone comprises at least one compressor and at least one separation vessel. An embodiment of the invention is one, any or all of prior embodiments in this paragraph up through the first embodiment in this paragraph further comprising transferring heat, in at least one heat exchanger, from the compressed overhead stream to a first exchanger stream. An embodiment of the invention is one, any or all of prior embodiments in this paragraph up through the first embodiment in this paragraph further comprising splitting the compressed overhead stream into at least a first portion and a second portion; transferring heat, in a first heat exchanger, from the first portion of the compressed overhead stream to a first exchanger stream; and, transferring heat, in a second heat exchanger, from the second portion of the compressed overhead stream to a second exchanger stream. An embodiment of the invention is one, any or all of prior embodiments in this paragraph up through the first embodiment in this paragraph further comprising condensing, in a condenser, the first portion and the second portion, after heat has been transferred from the first portion and the second portion, to provide a condensed stream; separating, in a receiver vessel, the condensed stream into a fuel gas stream and at least one liquid stream. An embodiment of the invention is one, any or all of prior embodiments in this paragraph up through the first embodiment in this paragraph further comprising transferring heat, in a third heat exchanger, from the first portion of the compressed overhead stream to a third exchanger stream, downstream of the first exchanger; and, transferring heat, in a fourth heat exchanger, from the second portion of the compressed overhead stream to a fourth exchanger stream, downstream of the second exchanger. An embodiment of the invention is one, any or all of prior embodiments in this paragraph up through the first embodiment in this paragraph further comprising condensing, in a condenser, the compressed overhead stream, after heat has been transferred from the compressed overhead stream, to provide a condensed stream; separating, in a receiver vessel, the condensed stream into a fuel gas stream and at least one liquid stream. An embodiment of the invention is one, any or all of prior embodiments in this paragraph up through the first embodiment in this paragraph wherein the receiver vessel also receives a liquid phase of the compressed overhead stream. An embodiment of the invention is one, any or all of prior embodiments in this paragraph up through the first embodiment in this paragraph further comprising recycling the at least one liquid stream from the receiver vessel to the toluene methylation zone.

A second embodiment of the invention is a process for para-xylene separation, the process comprising passing a toluene stream to a toluene methylation zone; passing a methanol stream to the toluene methylation zone, the toluene methylation zone operated under conditions to convert toluene to para-xylene and provide a methylated effluent comprising para-xylene and toluene; passing the methylated effluent to a fractionation column configured to separate the methylated effluent into at least an effluent stream comprising para-xylene, a recycle stream comprising toluene, and an overhead stream; passing the effluent stream comprising para-xylene to a para-xylene recovery zone configured to provide a para-xylene product stream; and passing the overhead stream to a compression zone configured to compress the overhead stream and provide a compressed overhead stream; and, passing the compressed overhead stream to a heat recovery zone configured to remove heat from the compressed overhead stream in at least one heat exchanger. An embodiment of the invention is one, any or all of prior embodiments in this paragraph up through the second embodiment in this paragraph, wherein the heat recovery zone includes a plurality of heat exchangers. An embodiment of the invention is one, any or all of prior embodiments in this paragraph up through the second embodiment in this paragraph, wherein the compressed overhead stream is passed to a compression zone comprising a compressor and a vessel before passing the compressed overhead stream to the heat recovery zone. An embodiment of the invention is one, any or all of prior embodiments in this paragraph up through the second embodiment in this paragraph further comprising splitting the compressed overhead stream into a plurality of compressed overhead streams; and, passing each compressed overhead stream from the plurality of compressed overhead streams to at least one heat exchanger. An embodiment of the invention is one, any or all of prior embodiments in this paragraph up through the second embodiment in this paragraph, wherein each compressed overhead stream from the plurality of overhead streams is passed to at least two heat exchangers. An embodiment of the invention is one, any or all of prior embodiments in this paragraph up through the second embodiment in this paragraph further comprising after removing heat from the compressed overhead stream in at the least one heat exchanger in the heat recovery zone, passing the compressed overhead stream to a condenser to provide a condensed stream; and, passing the condensed stream to a receiver vessel configured to separate the condensed stream into a fuel gas stream, at least one stream, and at least one liquid hydrocarbon stream. An embodiment of the invention is one, any or all of prior embodiments in this paragraph up through the second embodiment in this paragraph further comprising recycling the at least one liquid hydrocarbon stream to the toluene methylation zone.

A third embodiment of the invention is an apparatus for separating para-xylene from toluene, the apparatus comprising a fractionation column comprising an inlet and a plurality of outlets, the fractionation column being configured to receive, via the inlet, a stream comprising toluene and para-xylene, to separate the stream, and to provide at least an effluent stream comprising para-xylene via a first outlet from the plurality of outlets, a recycle stream comprising toluene via a second outlet from the plurality of outlets, and an overhead stream via a third outlet from the plurality of outlets; a compression zone having configured to compress the overhead stream to provide a compressed overhead stream; and, a heat recovery zone comprising at least one heat exchanger configured to remove heat from the compressed overhead stream. An embodiment of the invention is one, any or all of prior embodiments in this paragraph up through the third embodiment in this paragraph wherein the heat recovery zone further comprises a plurality of heat exchangers. An embodiment of the invention is one, any or all of prior embodiments in this paragraph up through the third embodiment in this paragraph, further comprising a first conduit configured to pass a first portion of the compressed overhead stream to a first heat exchanger; and, a second conduit configured to pass a second portion of the compressed overhead stream to a second heat exchanger. An embodiment of the invention is one, any or all of prior embodiments in this paragraph up through the third embodiment in this paragraph where in the compression zone comprises at least two compressors and a vessel.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for para-xylene separation, the process comprising:
    alkylating, in a toluene methylation zone, toluene with methanol to provide a methylated effluent comprising para-xylene and toluene;
    separating, in a fractionation column, the methylated effluent into at least an effluent stream comprising para-xylene, a recycle stream comprising toluene, and an overhead stream comprising $C_1$-$C_6$ hydrocarbons;
    recovering para-xylene from the effluent stream comprising para-xylene in a para-xylene recovery zone;
    compressing, in a first compression zone, the overhead stream to provide a compressed overhead stream; and
    after the overhead stream has been compressed, transferring heat from the compressed overhead stream.

2. The process of claim 1 further comprising:
    before transferring heat from the compressed overhead stream, compressing the compressed overhead stream in a second compression zone, wherein the second compression zone comprises at least one compressor and at least one separation vessel.

3. The process of claim 1 further comprising:
    transferring heat, in at least one heat exchanger, from the compressed overhead stream to a first exchanger stream.

4. The process of claim 1 further comprising:
    splitting the compressed overhead stream into at least a first portion and a second portion;
    transferring heat, in a first heat exchanger, from the first portion of the compressed overhead stream to a first exchanger stream; and
    transferring heat, in a second heat exchanger, from the second portion of the compressed overhead stream to a second exchanger stream.

5. The process of claim 4 further comprising:
    condensing, in a condenser, the first portion and the second portion, after heat has been transferred from the first portion and the second portion, to provide a condensed stream; and
    separating, in a receiver vessel, the condensed stream into a fuel gas stream and at least one liquid stream.

6. The process of claim 4 further comprising:
    transferring heat, in a third heat exchanger, from the first portion of the compressed overhead stream to a third exchanger stream, downstream of the first exchanger; and
    transferring heat, in a fourth heat exchanger, from the second portion of the compressed overhead stream to a fourth exchanger stream, downstream of the second exchanger.

7. The process of claim 1 further comprising:
    condensing, in a condenser, the compressed overhead stream, after heat has been transferred from the compressed overhead stream, to provide a condensed stream; and
    separating, in a receiver vessel, the condensed stream into a fuel gas stream and at least one liquid stream.

8. The process of claim 7 wherein the receiver vessel also receives a liquid phase of the compressed overhead stream.

9. The process of claim 7 further comprising:
    recycling the at least one liquid stream from the receiver vessel to the toluene methylation zone.

10. A process for para-xylene separation, the process comprising:
    passing a toluene stream to a toluene methylation zone;
    passing a methanol stream to the toluene methylation zone, the toluene methylation zone operated under conditions to convert toluene to para-xylene and provide a methylated effluent comprising para-xylene and toluene;
    passing the methylated effluent to a fractionation column configured to separate the methylated effluent into at least an effluent stream comprising para-xylene, a recycle stream comprising toluene, and an overhead stream;
    passing the effluent stream comprising para-xylene to a para-xylene recovery zone configured to provide a para-xylene product stream;
    passing the overhead stream to a compression zone configured to compress the overhead stream and provide a compressed overhead stream; and
    passing the compressed overhead stream to a heat recovery zone configured to remove heat from the compressed overhead stream in at least one heat exchanger.

11. The process of claim 10, wherein the heat recovery zone includes a plurality of heat exchangers.

12. The process of claim 11, wherein the compressed overhead stream is passed to a compression zone comprising a compressor and a vessel before passing the compressed overhead stream to the heat recovery zone.

13. The process of claim 10 further comprising:
    splitting the compressed overhead stream into a plurality of compressed overhead streams; and passing each compressed overhead stream from the plurality of compressed overhead streams to at least one heat exchanger.

14. The process of claim 13, wherein each compressed overhead stream from the plurality of overhead streams is passed to at least two heat exchangers.

15. The process of claim 10 further comprising:
after removing heat from the compressed overhead stream in at the least one heat exchanger in the heat recovery zone, passing the compressed overhead stream to a condenser to provide a condensed stream; and
passing the condensed stream to a receiver vessel configured to separate the condensed stream into a fuel gas stream, at least one stream, and at least one liquid hydrocarbon stream.

16. The process of claim 15 further comprising:
recycling the at least one liquid hydrocarbon stream to the toluene methylation zone.

\* \* \* \* \*